US005874433A

United States Patent [19]
Gross

[11] Patent Number: 5,874,433
[45] Date of Patent: *Feb. 23, 1999

[54] BLOCKING UTILIZATION OF TETRAHYDROBIOPTERIN TO BLOCK INDUCTION OF NITRIC OXIDE SYNTHESIS

[75] Inventor: Steven S. Gross, New York, N.Y.

[73] Assignee: Cornell Research Foundation, Inc., Ithaca, N.Y.

[ * ] Notice: The term of this patent shall not extend beyond the expiration date of Pat. No. 5,502,050.

[21] Appl. No.: 574,654

[22] Filed: Dec. 19, 1995

Related U.S. Application Data

[62] Division of Ser. No. 158,829, Nov. 29, 1993, Pat. No. 5,502,050.

[51] Int. Cl.$^6$ .......................... A01N 43/66; A61K 31/53; A61K 31/495
[52] U.S. Cl. .......................... 514/241; 514/249; 514/245; 514/246; 514/248; 514/256; 514/562; 514/563; 514/564; 514/565; 514/185; 514/186; 514/187; 544/257; 544/258; 544/259; 544/260; 544/261
[58] Field of Search .................................. 514/245, 246, 514/247, 248, 249, 256, 562, 563, 564, 565, 885, 886, 185, 186, 187, 241; 544/257, 258, 259, 260, 261

[56] References Cited

U.S. PATENT DOCUMENTS

| | | | |
|---|---|---|---|
| 3,382,247 | 5/1968 | Anthony | 544/321 |
| 3,557,106 | 1/1971 | Roch | 544/260 X |
| 3,644,364 | 2/1972 | Anthony | 544/323 |
| 4,670,438 | 6/1987 | Austel et al. | 514/249 |
| 4,701,455 | 10/1987 | Nichol et al. | 514/249 |
| 5,002,944 | 3/1991 | Spada et al. | 514/221 |
| 5,028,627 | 7/1991 | Kilbourn et al. | 514/565 |
| 5,059,712 | 10/1991 | Griffith | 562/560 |
| 5,132,453 | 7/1992 | Griffith | 562/560 |
| 5,158,883 | 10/1992 | Griffith | 435/240.2 |
| 5,196,195 | 3/1993 | Griffith | 424/94.6 |
| 5,216,025 | 6/1993 | Gross et al. | 514/565 |
| 5,273,875 | 12/1993 | Griffith | 435/1 |
| 5,281,627 | 1/1994 | Griffith | 514/565 |
| 5,298,506 | 3/1994 | Stamler et al. | 514/226.2 |
| 5,401,844 | 3/1995 | Ayling et al. | 544/320 |
| 5,449,668 | 9/1995 | Wahl et al. | 514/546 |

FOREIGN PATENT DOCUMENTS

| | | |
|---|---|---|
| 2075346 | 6/1993 | Canada . |
| 446699 | 9/1991 | European Pat. Off. . |
| WO8404040 | 10/1984 | WIPO . |

OTHER PUBLICATIONS

Ponzone et al. "catalytic activity of tetrahydrobiopterin in dihydropterine reductase defiency and indications for treatment". Pediatric Research. vol. 33, No. 2, pp. 125–128, 1993.

Gross, S.S.,et al,Biochem.Biophys.Res.Commun,178,No. 3,823–829 (Aug. 15, 1991).

Kaufman,S,et al, J.Biol.Chem.,234,No. 10,2683–2688(Oct. 1959).

Kaufman,S.,et al, J.Biol.Chem.,242,No. 17,3934–3943(Sep. 1967).

Kerler,F.,et al, Exp.Cell Res.,189,151–156(1990).

Kwon,N.S.,et al,J.Biol.Chem.,264,No. 34,20496–20501(Dec. 1989).

Milstien,S.,et al,Biochem.Biophys.Res.Commun.,128,No. 3,1099–1107(May 1985).

Nichol,C.,et al, Ann.Rev.Biochem.54,729–764(1985).

Tayeh,M.A., et al.J.Biol.Chem.,264,No. 33,19654–19658(1989).

Werner–Felmayer,G.,et al. J.Exp.Med.,172, 1599–1607(1990).

Ziegler,I.,et al, J.Biol.Chem.,265,No. 28,17026–17030(Oct. 1990).

Marletta, M.A., "Nitric oxide: biosynthesis and biological significance," name of publication unknown, Elsevier Science Publishers, Ltd. (UK), pp. 448–453 (1989).

Book of Abstracts, Second International Meeting Biology of Nitric Oxide, cover page, meeting schedule page, abstract headed Oct. 1991.

Synthesis of Tetrahydrobiopterin is a Requirement for Induction of Nitric Oxide Synthesis by LPS/Interferon in Vascular Smooth Muscle (Steven S. Gross and Roberto Levi).

Werner, E., et al, Biochem. J., 262:861–866(1989).

Moncada, S., et al, Pharmacological Reviews 43(2):109–142 (1991).

Gross, S.S., et al, Biochem. Biophys. Res. Commun. 170, 96–103 (Jul. 1990).

Gross, S.S., et al, J. Biol. Chem. 267, 25722–25729 (Dec. 1992).

(List continued on next page.)

Primary Examiner—Marian Knode
Assistant Examiner—Datquan Lee

[57] ABSTRACT

Inhibitor of the use of tetrahydrobiopterin as a cofactor for nitric oxide synthase, e.g., substituted 4-phenyl (hydropyridines) such as 1-methyl-4-(3',4'-dihydroxyphenyl)-1,2,3,6-tetrahydropyridine or, 4-(3',4'-dihydroxyphenyl)-1,2,3,6-tetrahydropyridine) or tetrahydropterin analog which does not replace tetrahydrobiopterin as a substrate for nitric oxide synthase such as (6R,S)-6,7-dimethyl-tetrahydropterin or (6R,S)-tetrahydrofolic acid or 2,4-diamino-, 2,6-diamino, or 4,6-diamino mono- or disubstituted pyrimidines or the corresponding pyrimidine-3-oxides such as 2,4-diamino-6-(diethylamino)pyrimidine, 2,4-diamino-6-piperidino-pyrimidine-3-oxide, 2,4-diamino-6-hydroxypyrimidine, 4,6-diamino-2-hydroxypyrimidine or 2,5-diamino-4,6-dihydroxypyrimidine is administered to inhibit nitric oxide synthesis from arginine in vascular cells in a subject in need of such inhibition (e.g., for prophylaxis or treatment of cytokine- or endotoxin-induced hypotension (e.g., septic shock). The latter two types are advantageously administered with nitric oxide synthase inhibitors (concurrent therapy) or to potentiate the effect of $\alpha_1$-adrenergic agonists in the prophylaxis or treatment of induced hypotension.

15 Claims, 9 Drawing Sheets

OTHER PUBLICATIONS

Kilbourn, R.G., et al, Biochem. Biophys. Res. Commun. 172, 1132–1138 (Nov. 1990).

Kilbourn, R.G., et al, J. Natl. Cancer Inst. 84, 827–831 (Jun. 1992).

Collier, Jr., et al, Trends in Pharmacological Sciences Including Toxicological Sciences, Elsevier Science Publishers, Ltd., published in UK 1989, frontpage and pages 428–431.

Kilbourn, R.G., et al, Proc. Natl. Acad. Sci. U.S.A, 87, 3629–3632, 1990.

McCall, J.M., et al, J. Org. Chem., 40, No. 22, 3304–3306, 1975.

Rees, D.D., et al, Br. J. Pharmacol., 96, 418–424 (1989).

Rees, D.D., et al, Nitric oxide from L–arginine: a bioregulatory system, S. Moncada et al eds., Elsevier Science Publishers, BV, 485–487 (1990).

Gessner, W., et al, J. Med. Chem., 28, 311–317 (1985).

Vallance, P., et al, New Horizons, 77–86 (Feb. 1993).

Rees, D.D., et al, Br. J. Pharmacol., 101, 746–752 (1992).

Stuehr, D.J., et al, Advances in Enzymology 65, 287–346 (1992).

Gross, S., et al, FASEB Journal 6, A1509, 1992.

Gross, S., J. Vasc. Res., 29, 125–126, Abstract 147, 1992.

Gray, G.A., et al, Br. J. Pharmacol., 103, 1218–1224 (May 1991).

Aisaka, K., et al, Biochem. Biophys. Res. Commun. 163, No. 2, 710–717 (Sep. 15, 1989).

Julou–Schaeffer, G., et al, Am. J. Physiol. 259, H10-38–H1043, Oct. 1990.

Giovanelli, J., et al, Medline Abstract of Proc. Nat'l. Acad. Sci. USA 88(16), 7091–7095 (Aug. 1991).

Abell, C.W., et al., Science, vol. 224, 405–407, Apr. 1984.

Craine, J. E., et al., J. Biol. Chem, vol. 247, No. 19, 6082–6091 (1972).

5,874,433

BLOCKING UTILIZATION OF TETRAHYDROBIOPTERIN TO BLOCK INDUCTION OF NITRIC OXIDE SYNTHESIS

This is a divisional of application Ser. No. 08/158,829 filed on Nov. 29, 1993, now U.S. Pat. No. 5,502,050.

This invention was made at least in part with Government support under Grant HL46403 from the National Institutes of Health.

TECHNICAL FIELD

This invention is directed to a novel method of inhibiting the induction of nitric oxide formation in biological systems by bacterial endotoxins and cytokines.

BACKGROUND OF THE INVENTION

For several decades nitroglycerin has been administered to humans as a vasodilating agent in the treatment of cardiovascular disease. Recently, it has been shown that nitroglycerin so administered is converted in the body to nitric oxide which is the pharmacologically active metabolite. Still more recently, nitric oxide has been shown to be formed enzymatically from arginine as a normal metabolite which is an important component of endothelium-derived relaxing factors (EDRFs). EDRFs are currently being intensively studied as participating in regulation of blood flow and vascular resistance. In addition to vascular endothelium, macrophages have also been shown to produce nitric oxide in the body which is a component of their cell killing and/or cytostatic function.

It has been established that the enzyme forming nitric oxide from arginine, i.e., nitric oxide synthase, occurs in two distinct types, namely the constitutive forms and an inducible form. Constitutive forms are present in normal endothelial cells, neurons and some other tissues. Formation of nitric oxide by constitutive form in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension. Furthermore, it is thought that overproduction of nitric oxide by the inducible form of nitric oxide synthase is a basis for insensitivity to pressor agents such as $\alpha_1$-adrenergic agonists used in the treatment of septic or cytokine-induced shock patients.

Considerable research effort has been expended to discover inhibitors for nitric oxide synthase activity. In large measure, said research effort has been directed at uncovering arginine analogs which inhibit nitric oxide synthase activity by blocking the use of arginine as substrate for nitric oxide synthase.

SUMMARY OF THE INVENTION

The broad invention herein does not rely on arginine antagonists but rather uses a novel approach to selectively block the induction of nitric oxide synthesis by cytokines and/or microbial products (e.g., bacterial endotoxins).

The invention herein relies on the recent discovery that tetrahydrobiopterin is a required cofactor for nitric oxide in the conversion of arginine to citrulline and nitric oxide in induced nitric oxide synthesis (i.e., in nitric oxide synthesis induced by cytokines and/or microbial products).

It has been discovered herein that inhibiting the use of tetrahydrobiopterin as a cofactor for nitric oxide synthase in vascular cells inhibits the induction of nitric oxide synthesis in said cells by bacterial endotoxins and cytokines (e.g., interferons including interferon-gamma, tumor necrosis factor, interleukin-1 and interleukin-2), i.e., performs such inhibiting without affecting physiological constitutive enzyme-mediated nitric oxide synthesis.

One embodiment of the invention herein is directed at a method of prophylaxis or treatment of a subject for systemic hypotension caused by pathological overproduction of nitric oxide from arginine in vascular cells in said subject induced by therapy with a cytokine, e.g., interferons including gamma-interferon, tumor necrosis factor, interleukin-1 or interleukin-2, e.g., chemotherapeutic treatment with tumor necrosis factor or interleukin-2, or exposure to a bacterial endotoxin (i.e., septic shock), e.g., from bacterial infection or arising from immunosuppression therapy, said method comprising administering to said subject possibly developing or having such systemic hypotension, a therapeutically effective amount of at least one inhibitor of the use of tetrahydrobiopterin as a cofactor for nitric oxide synthase.

Preferred inhibitors of the use of tetrahydrobiopterin as a cofactor for nitric oxide synthase include dihydroxy substituted 4-phenyl(hydro)pyridines and the corresponding quinones and semiquinones, tetrahydropterin analogs which do not replace tetrahydrobiopterin as a cofactor for nitric oxide synthase and 2,4-diamino-, 4,6-diamino, and 2,5-diamino mono- and disubstituted pyrimidines and the corresponding pyrimidine-3-oxides.

A second embodiment of the invention herein is directed at a method of prophylaxis or treatment of a subject for systemic hypotension caused by pathological overproduction of nitric oxide from arginine in vascular cells in said subject induced by therapy with a cytokine, e.g., interferons including interferon-gamma, tumor necrosis factor, interleukin-1 or interleukin-2, e.g., chemotherapeutic treatment with tumor necrosis factor or interleukin-2, or exposure to bacterial endotoxin (i.e., septic shock), e.g., from bacterial infection or arising from immunosuppression therapy, said method involving administering to a subject possibly developing or having such systemic hypotension, a pressor agent such as an $\alpha_1$-adrenergic agonist, e.g., phenylephrine, epinephrine, norepinephrine, dopamine, metaraminol, methoxamine, ephedrine, and mephentermine, in a therapeutically effective amount (i.e., in an amount to increase blood pressure), and a therapeutically effective amount of at least one inhibitor of the use of tetrahydrobiopterin as a cofactor for nitric oxide synthase selected from the group consisting of tetrahydropterin analogs which do not replace tetrahydrobiopterin as a cofactor for nitric oxide synthase and 2,4-diamino-, 4,6-diamino- and 2,5-diamino mono- and disubstituted pyrimidines and the corresponding pyrimidine-3-oxides, i.e, an amount of said inhibitor to restore vascular sensitivity to the effects of the pressor agents thereby to increase and/or to prolong the efficacy of the $\alpha_1$-adrenergic agonists, i.e, to potentiate the effectiveness of the $\alpha_1$-adrenergic agonists.

A third embodiment of the invention herein is directed to prophylaxis or treatment of a subject for systemic hypotension caused by pathological overproduction of nitric oxide from arginine in vascular cells in said subject induced by therapy with a cytokine, e.g., interferons including interferon-gamma, tumor necrosis factor, interleukin-1 or interleukin-2, e.g., chemotherapeutic treatment with tumor necrosis factor or interleukin-2, or exposure to bacterial endotoxin (i.e., septic shock), e.g., from bacterial infection or arising from immunosuppression therapy, said method involving administering to a subject possibly developing or having such systemic hypotension a therapeutically effective amount (i.e., a nitric oxide production limiting, blood pressure raising, amount) of a nitric oxide synthase inhibitor, e.g., arginine or citrulline analogs including $N^G$-methyl-L-arginine, $N^G$-amino-L-arginine, $N^G$-nitro-L-arginine, $N^G$-nitro-L-arginine methyl ester, $N^\delta$-iminomethyl-L-ornithine, or canavanine, and a therapeutically effective amount (i.e., a nitric oxide production limiting, blood pressure raising, amount) of at least one inhibitor of the use of tetrahydrobiopterin as a cofactor for nitric oxide synthase selected from the group consisting of tetrahydropterin analogs which do not replace tetrahydrobiopterin as a cofactor for nitric oxide synthase and 2,4-diamino-, 4,6-diamino-, and 2,5-diamino mono- and disubstituted pyrimidines and the corresponding pyrimidine-3-oxides.

The term "subject" is used herein to mean any mammal, including humans, where nitric oxide formation from arginine occurs. The method herein for use on subjects contemplates prophylactic use as well as curative use in therapy of an existing condition.

The term "4-phenyl(hydro)pyridines" is used herein to include 4-phenylpyridine, 4-phenylpiperidine and 4-phenyltetrahydropyridine.

The term "which do not replace tetrahydrobiopterin as a cofactor for nitric oxide synthase" means no more than 15% of the nitric oxide synthase activity observed with the 6R isomer of tetrahydrobiopterin under the conditions for testing this in Example VI.

DETAILED DESCRIPTION

Figure 1:
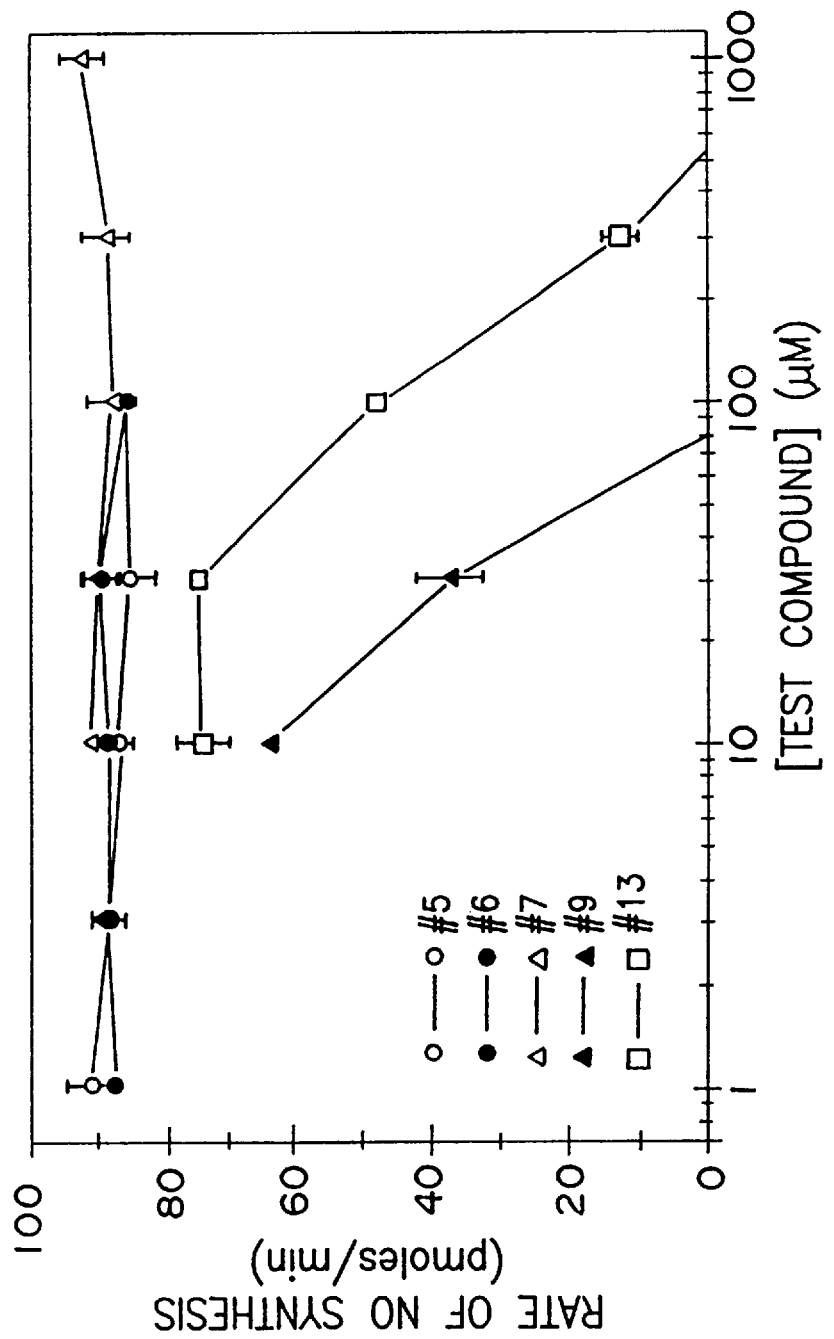
FIG. 1 depicts graphs of rate of nitric oxide (denoted NO) synthesis versus 4-phenyltetrahydropyridine concentration for five 4-phenyltetrahydropyridines (denoted Compounds #5, #6, #7, #9 and #13) and shows results of Example I.

We turn firstly to the inhibitors of the use of tetrahydrobiopterin as a cofactor for nitric oxide synthase that are substituted 4-phenyl(hydro)pyridine compounds.

These include, for example, those with the structural formula

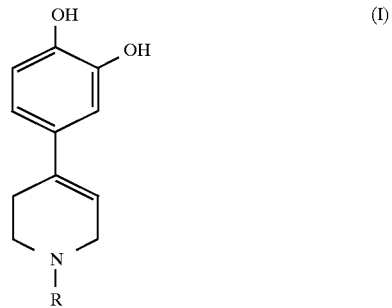

(I)

wherein R is selected from the group consisting of hydrogen and halogen (fluorine, chlorine, bromine and iodine) atoms, and $C_{1-6}$ alkyl, $C_{1-6}$ halo (fluoro, chloro, bromo, iodo) alkyl and $C_{2-6}$ acyl groups, pharmaceutically acceptable acid addition salts of the compounds of the formula (I), those with the structural formula II

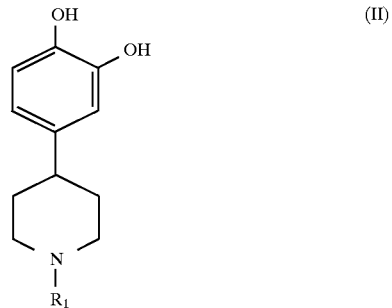

(II)

wherein $R_1$ is selected from the group consisting of hydrogen and halogen (fluorine, chlorine, bromine and iodine atoms and $C_{1-6}$ alkyl, $C_{1-6}$ halo (fluoro, chloro, bromo, iodo) alkyl and $C_{2-6}$ acyl groups, pharmaceutically acceptable acid addition salts of the compounds of the structural formula (II), that with the structural formula (III)

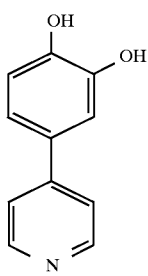

and N-oxide thereof, and compounds of the structural formula (IV)

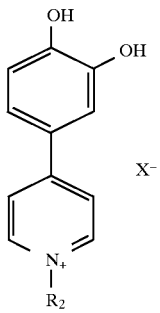

wherein $R_2$ is selected from the group consisting of hydrogen and halogen (fluorine, chlorine, bromine and iodine) atoms and $C_{1-6}$ alkyl, $C_{1-6}$ halo (fluoro, chloro, bromo, iodo) and $C_{2-6}$ acyl groups, and $X^-$ is a pharmaceutically acceptable balancing anion, e.g., bromo, chloro, methosulfate, bisulfate, bicarbonate, acetate, citrate or bitartrate, and the semiquinones and quinones corresponding to the compounds of formulas (I) and (II) and their pharmaceutically acceptable acid addition salts, and to the compounds of the formulas (III) and (IV).

Examples of compounds of structural formula (I) include that where R is methyl, i.e., 1-methyl-4-(3',4'-dihydroxyphenyl)-1,2,3,6-tetrahydropyridine, that where R is hydrogen, i.e., 4-(3',4'-dihydroxyphenyl)-1,2,3,6-tetrahydropyridine and that where R is acetyl, i.e., 1-acetyl-4-(3',4'-dihydroxyphenyl)-1,2,3,6-tetrahydropyridine. The synthesis of the hydrobromide salt of the compound where R is methyl, and of the hydrochrloride salt of the compound where R is hydrogen and of the compound where R is acetyl are described in Gessner, W., et al, J. Med. Chem., 28, 311–317 (1985). Homologous compounds to the one where R is methyl are prepared by substituting the appropriate 1-alkyl-4-piperidine for 1-methyl-4-piperidine in the synthesis described in Gessner et al. Homologous compounds to the one where R is acetyl are prepared by substituting the appropriate alkanoic acid for acetic acid in the synthesis described in Gessner et al. The compounds of formula (I) where R is haloalkyl are prepared by substituting the appropriate 1-haloalkyl-4-piperidine for the 1-methyl-4-piperidine in the synthesis described in Gessner et al.

Examples of compounds of the formula (II) include, for example, that where $R_1$ is methyl, i.e., 1-methyl-4-(3',4'-dihydroxyphenyl)piperidine, that where $R_1$ is hydrogen, i.e., 4-(3',4'-dihydroxyphenyl)piperidine and that where $R_1$ is acetyl, i.e., 1-acetyl-4-(3',4'-dihydroxyphenyl)piperidine. The synthesis of the hydrobromide salt of the compound where $R_1$ is methyl and of the hydrochloride salt of the compound where $R_1$ is hydrogen and of the compound where $R_1$ is acetyl are described in Gessner, W., et al, J. Med. Chem., 28, 311–317 (1985). Piperidines are obtained from corresponding tetrahydropyridines by reduction over Adam's catalyst in alkanoic acid via N-acyl analogs.

The compound of the formula (III) is 4-(3',4'-dihydroxyphenyl)pyridine and its synthesis is described in Gessner, W., et al, J. Med. Chem., 28, 311–317 (1985). The N-oxide of this is prepared by oxidizing pyridine precursor with a peracid (e.g., peracetic, performic, perbenzoic or peroxytrifluoroacetic acid).

An example of compounds of the formula (IV) is that where $R_2$ is methyl. The synthesis of this compound is described in Gessner, W., et al, J. Med. Chem., 28, 311–317 (1985). The quaternary ammonium compounds of formula (IV) are prepared from the compound of the formula (III) by reacting it with the appropriate quaternizing compound, e.g., halide or methosulfate.

Pharmaceutically acceptable acid addition salts include, for example, hydrochloride, hydrobromide, methosulfate, acetate, sulfate, phosphate, succinate, citrate and propionate acid addition salts.

The quinones and semiquinones are those where both hydroxys (quinone) or one hydroxy (semiquinone) are replaced with a ketone group with balancing change in the saturation in the ring to which they are pendant and are formed on solution of the dihydroxy compounds in water according to the applicable equilibrium equation.

We turn now to the inhibitors of the use of tetrahydrobiopterin as a cofactor for nitric oxide synthase which are tetrahydrobiopterin analogs which do not replace tetrahydrobiopterin as a substrate for nitric oxide synthase.

These include, for example, (6R,S)-6,7-dimethyltetrahydropterin, (6R,S)-tetrahydrofolic acid, 5-methyl-(6R,S)-tetrahydrofolic acid, 5,10-methenyl-(6R,S)-tetrahydrofolic acid and (6R,S)-$N^5,N^{10}$-methylenetetrahydrofolic acid. These are all available commercially.

We turn now to the inhibitors of the use of tetrahydrobiopterin as a cofactor for nitric oxide synthase which are selected from the group consisting of 2,4-diamino-, 4,6-diamino-, and 2,5-diamino- mono- and disubstituted pyrimidines and the corresponding pyrimidine-3-oxides.

These include 2,4-diamino-6-substituted pyrimidines, 2,4-diamino-5-substituted pyrimidines, 2,4-diamino-5,6-disubstituted pyrimidines, 2,5-diamino-4-substituted pyrimidines, 2,5-diamino-6-substituted pyrimidines, 2,5-diamino-4,6-disubstituted pyrimidines, 4,6-diamino-2-substituted pyrimidines, 4,6-diamino-5-substituted pyrimidines and 4,6-diamino-2,5-disubstituted pyrimidines and the corresponding pyrimidine-3-oxides. The 2,4-diamino-6-substituted pyrimidines and the 2,4-diamino-6-substituted-pyrimidine-3-oxides are preferred. Inhibition by this group of compounds can be overcome by increasing the amount of tetrahydrobiopterin in the system.

The substitution moiety (moieties) is (are) selected, for example, from the group consisting of $C_{1-6}$ alkyl, $C_{1-6}$ alkoxy, halo (e.g., chloro, bromo, fluoro or iodo), amino, mono- and di- $C_{1-6}$ haloalkyl (e.g., chloro, bromo, fluoro, or iodo), mono- and di- $C_{1-6}$ alkylamino, piperidino and hydroxy. Compounds with 6-morpholino substitution are not inhibitors.

Suitable inhibitors of the use of tetrahydrobiopterin as a cofactor for nitric oxide synthase which are selected from the group consisting of 2,4-diamino-, 4,6-diamino-, and 2,5-diamino- mono- and disubstituted pyrimidines and the corresponding pyrimidine-3-oxides include, for example, 2,4-diamino-6-(diethylamino)pyrimidine, 2,4-diamino-6-hydroxypyrimidine, 2,4-diamino-6-methylpyrimidine, 2,4-diamino-6-chloropyrimidine, 2,4-diamino-5-methyl-6-diethylaminopyrimidine, 2,5-diamino-4-hydroxypyrimidine, 2,5-diamino-6-hydroxypyrimidine, 2,5-diamino-4,6-dihydroxypyrimidine, 4,6-diamino-2-hydroxypyrimidine, 4,6-diamino-5-hydroxypyrimidine, 4,6- diamino-2,5-dihydroxypyrimidine and 2,4-diamino-6-piperidino-pyrimidine-3-oxide.

The 2,4-diamino-6-methyl pyrimidine is available commercially and the other 6-alkyls can be prepared by using homologous reactants and the 6-haloalkyls can be prepared by using analogous reactants. The 2,4-diamino-6-chloropyrimidine is available commercially and the other 6-halo compounds can be made using analagous reactants. The 2,4-diamino-6-hydroxypyrimidine is available commercially. The 6-2,4-diamino-6-piperidinopyrimidine-3-oxide is available commercially under the name Minoxidil®. The 2,4-diamino-6-alkylamino pyrimidines are readily prepared by reacting the appropriate amine with 2,4-diamino-6-chloropyrimidine. The 2,4-diamino-6-alkoxypyrimidines are readily prepared by substituting in the 2,4-diamino-6-hydroxypyrimidine. The 4,6-diamino-2-hydroxypyrimidine and the 2,5-diamino-4,6-dihydroxypyrimidine are commercially available and the other 4,6-diamino and 2,5-diamino compounds may be made analagously. For methods of preparation, see also Anthony U.S. Pat. No. 3,382,247 and Anthony U.S. Pat. No. 3,644,364. For methods of preparation for 6-substituted pyrimidines and the corresponding 3-oxides, see also Journal of Organic Chemistry, Vol. 40, No. 22, page 3305 (1975). In addition, other methods of preparation of the compounds of this group are obvious to those skilled in the art.

The dosages of the inhibitors of the use of tetrahydrobiopterin as a cofactor for nitric synthase generally range from 1 $\mu$g/kg to 500 mg/kg with the actual dosage depending on the inhibitor selected. For the inhibitors which are dihydroxy substituted 4-phenyl (hydro) pyridines and the corresponding quinones and semiquinones, a suitable dosage ranges, for example, from 1 $\mu$g/kg to 10 mg/kg. For the inhibitors which are tetrahydropterin analogs which do not replace tetrahydrobiopterin as a cofactor for nitric oxide synthase, a suitable dosage ranges, for example, from 0.1 to 100 mg/kg. For the inhibitions which are selected from the group consisting of 2,4-diamino-, 2,5-diamino and 4,6-diamino mono- and disubstituted pyrimidines and the corresponding pyrimidine-3-oxides, suitable dosages range, for example, from 1 to 500 mg/kg. Preferably, the said inhibitors are administered intravenously or by other route providing fast response, for the prophylaxis or treatment of systemic hypotension caused by overproduction of nitric oxide induced by therapy with cytokines and exposure to bacterial endotoxins. For other conditions where induced nitric oxide synthesis may be detrimental, e.g., in immune-rejection phenomena and neurodegenerative diseases, other methods of administration may also be appropriate, e.g., oral, intrasynovial, subcutaneous, or intramuscular methods of administration.

We turn now to the $\alpha_1$-adrenergic agonists. The $\alpha_1$-adrenergic agonists are currently used to treat hypotension in septic and cytokine treated patients but eventually stop working because of loss of vascular contractile sensitivity. They are used herein in the same dosages as they are currently used, i.e., in conventional therapeutically effective amounts. As indicated above, suitable $\alpha_1$-adrenergic agonists include, for example, epinephrine, norepinephrine, dopamine, phenylephrine, metaraminol, methoxamine, ephedrine, and mephentermine. Doses for dopamine typically range from 2 $\mu$g/kg/min to 50 $\mu$g/kg/min. Doses for epinephrine typically range from 0.25 mg to 1.0 mg. Doses for norepinephrine typically range from 2 $\mu$g/min to 4 $\mu$g/min and are typically used if dopamine dose exceeds 20 $\mu$g/kg/min. Doses for phenylephrine can range from 0.1 to 10 $\mu$g/kg. The route of administration of the most popular $\alpha_1$-adrenergic agonists (epinephrine, norepinephrine and dopamine) is intravenous and for the others the route of administration is intravenous or in some cases subcutaneous.

We turn now to the nitric oxide synthase inhibitors. The dosages of these generally range from 0.1 to 100 mg/kg, with the actual dosage depending on the inhibitor selected. Doses for $N^G$-methyl-L-arginine range from 1 to 40 mg/kg. The route of administration is preferably intravenous or other route providing a fast response.

Figure 5:
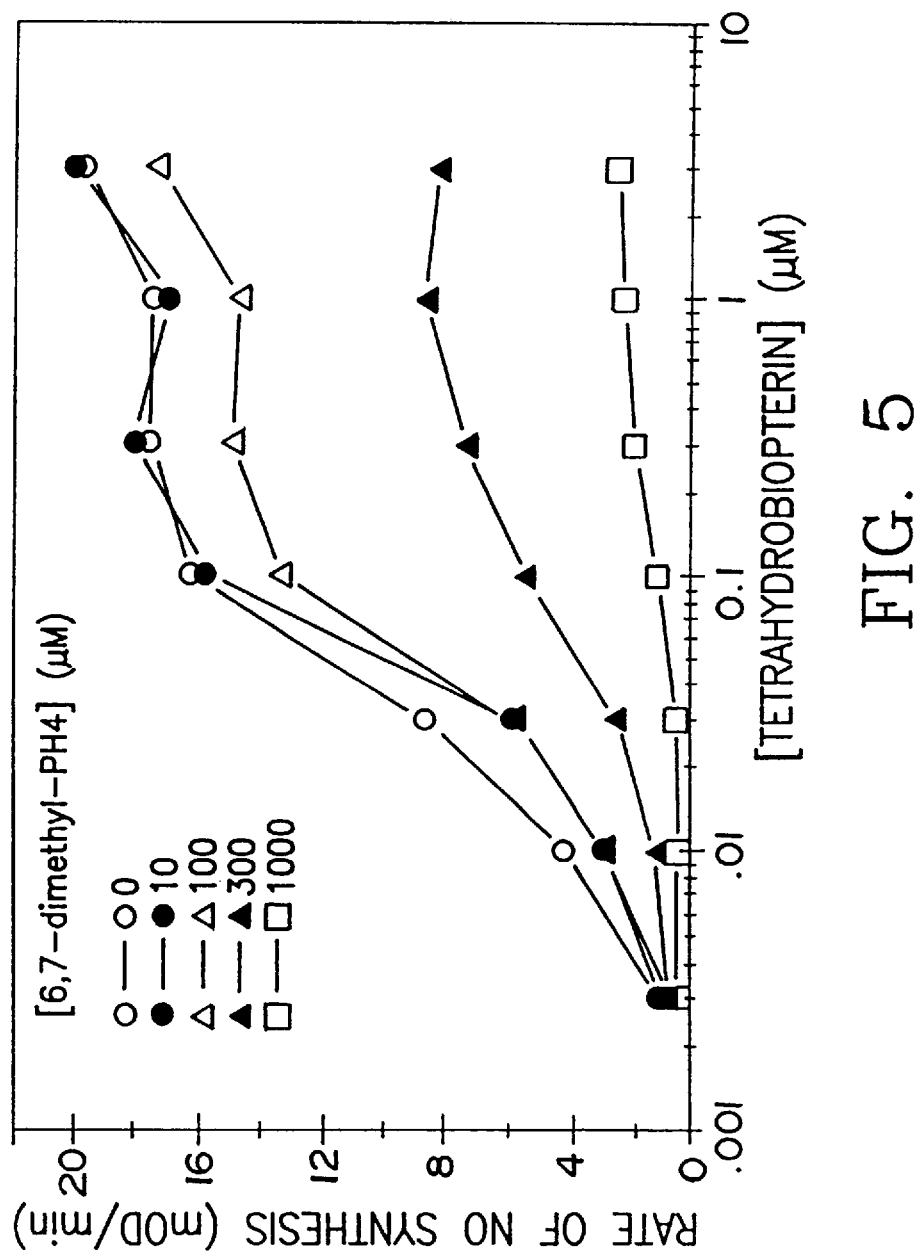
FIG. 5 depicts graphs of rate of nitric oxide (denoted NO) synthesis versus tetrahydrobiopterin (denoted $BH_4$) concentration for denoted concentrations of (6R,S)-6,7-dimethyltetrahydropterin (denoted 6,7-dimethyl-PH4) and shows results of Example VI.
Figure 6:
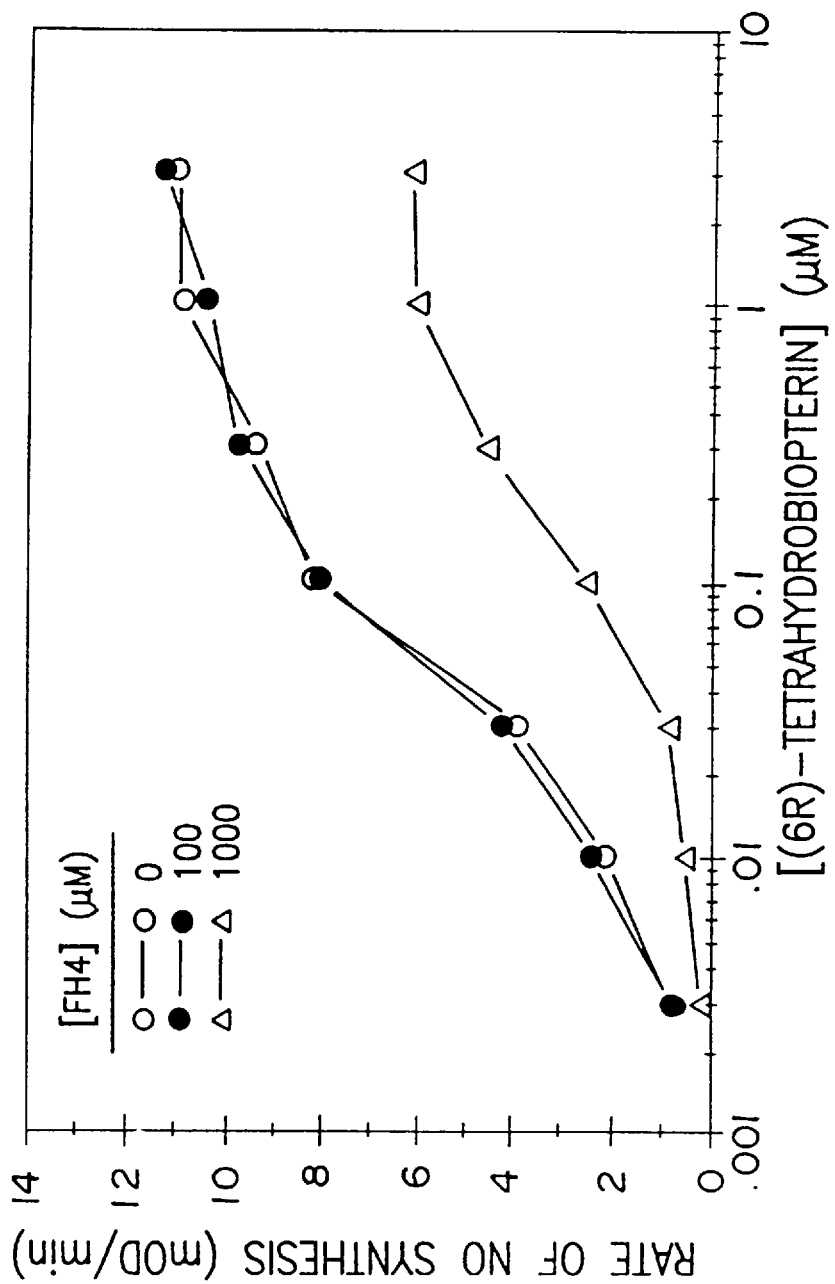
FIG. 6 depicts graphs of rate of nitric oxide (denoted NO) synthesis versus tetrahydrobiopterin (denoted (6R)-tetrahydrobiopterin) concentrations for denoted concentrations of tetrahydrofolic acid (denoted $FH_4$) and shows results of Example VI.
Figure 9:
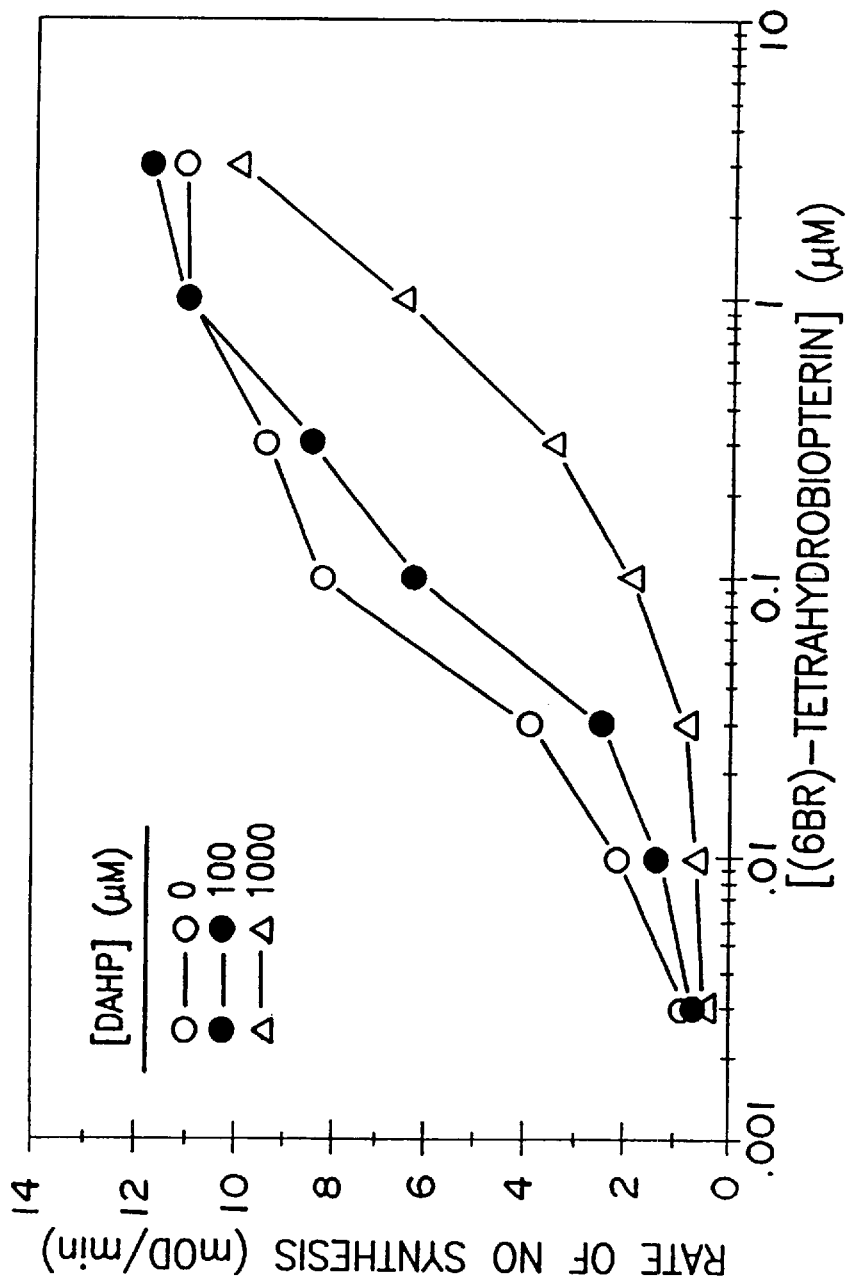
FIG. 9 depicts graphs of rate of nitric oxide (denoted NO) synthesis versus tetrahydrobiopterin concentration for denoted concentrations of 2,4-diamino-6-hydroxypyrimidine (denoted DAHP) and shows results of Example X.

The following examples are illustrative of the concepts of the invention and represent the best mode known to the inventor at this time. Results of some of the examples are set forth in figures in terms of mOD/min (FIGS. 5, 6 and 9). The unit mOD/min. is a reading from the particular instrument used to measure rate of nitric oxide synthesis in Examples VI and X, i.e., the kinetic microplate reader described in Example I; 1 mOD/min equals about 10 pmoles/min.

EXAMPLE I

Purified induced nitric oxide synthase enzyme is obtained as described in Bredt and Snyder, PNAS, 87, 682–685 (1990) by harvesting cultured rat aortic smooth muscle cells after activation with interferon-gamma (50 ng/ml) and *Eschericia coli* lipopolysaccharide (30 $\mu$g/ml), lysing the harvested cells by freezing in liquid nitrogen and thawing by incubation in a 37° C. water bath, preparing a cell cytosal by centrifugation of the cell lysate at 120,000×g and purifying by affinity chromatography on 2',5'-ADP-Sepharose resin.

The purified enzyme is dissolved in 80 mM Tris buffer, pH 7.6 (100 $\mu$g protein/ml).

Reaction medium is then made up containing 0.1 ml of the enzyme composition (1 $\mu$g protein), 500 $\mu$M L-arginine, 500 $\mu$M nicotinamide adenine dinucleotide phosphate (reduced form), 10 $\mu$M flavin adenine dinucleotide, 10 $\mu$M tetrahydrobiopterin and varying concentrations of 1-methyl-4-(4'-hydroxyphenyl)-1,2,3,6-tetrahydropyridine (referred to in FIG. 1 as compound #5), 1-methyl-4-(3'-methoxy-4'-hydroxyphenyl)-1,2,3,6-tetrahydropyridine (referred to in FIG. 1 as compound #6), 4-(4'-hydroxyphenyl)-1,2,3,6-tetrahydropyridine (referred to in FIG. 1 as compound #7), 1-methyl-4-(3',4'-dihydroxyphenyl)-1,2,3,6-tetrahydropyridine (referred to in FIG. 1 as Compound #9), and 4-(3',4'-dihydroxyphenyl)-1,2,3,6-tetrahydropyridine (referred to in FIG. 1 as Compound #13). The compounds #5, #6, #7, #9 and #13 were prepared as described in Gessner, W., et al, J. Med. Chem. 28, 311–317 (1985). Assaying for nitric oxide was carried out based on the ability of nitric oxide to oxidize ferrous myoglobin to ferric myoglobin with accompanying change in optical density at 405–650 nm. The reduced myoglobin is prepared by reducing 2 mM myoglobin (from horse skeletal muscle, Sigma) with an excess of sodium dithionite and immediately applying the resulting composition to a Syphadex G-25 column, followed by elution with 50 mM Tris buffer, pH 7.6, aliquoting and storing at −70° C. for up to 2 months prior to use. The progress of the oxidation is continuously measured in a kinetic microplate reader (Molecular Devices, Menlo Park, Calif.) as the rate of change in optical density at 405–650 nm. Data points are collected every 16 seconds for 20 minutes at 25° C. and the slope of the best fit regression line is used to calculate the rate of nitric oxide synthesis in pmoles/min.

The results are shown in FIG. 1.

As shown in FIG. 1, Compound #9 and Compound #13 are potent inhibitors of purified induced nitric oxide synthase. As shown in FIG. 1, Compound #5, Compound #6 and Compound #7, which are not 3,4-dihydroxy compounds or the corresponding quinones or semiquinones are not inhibitors of purified induced nitric oxide synthase.

EXAMPLE II

Figure 2:
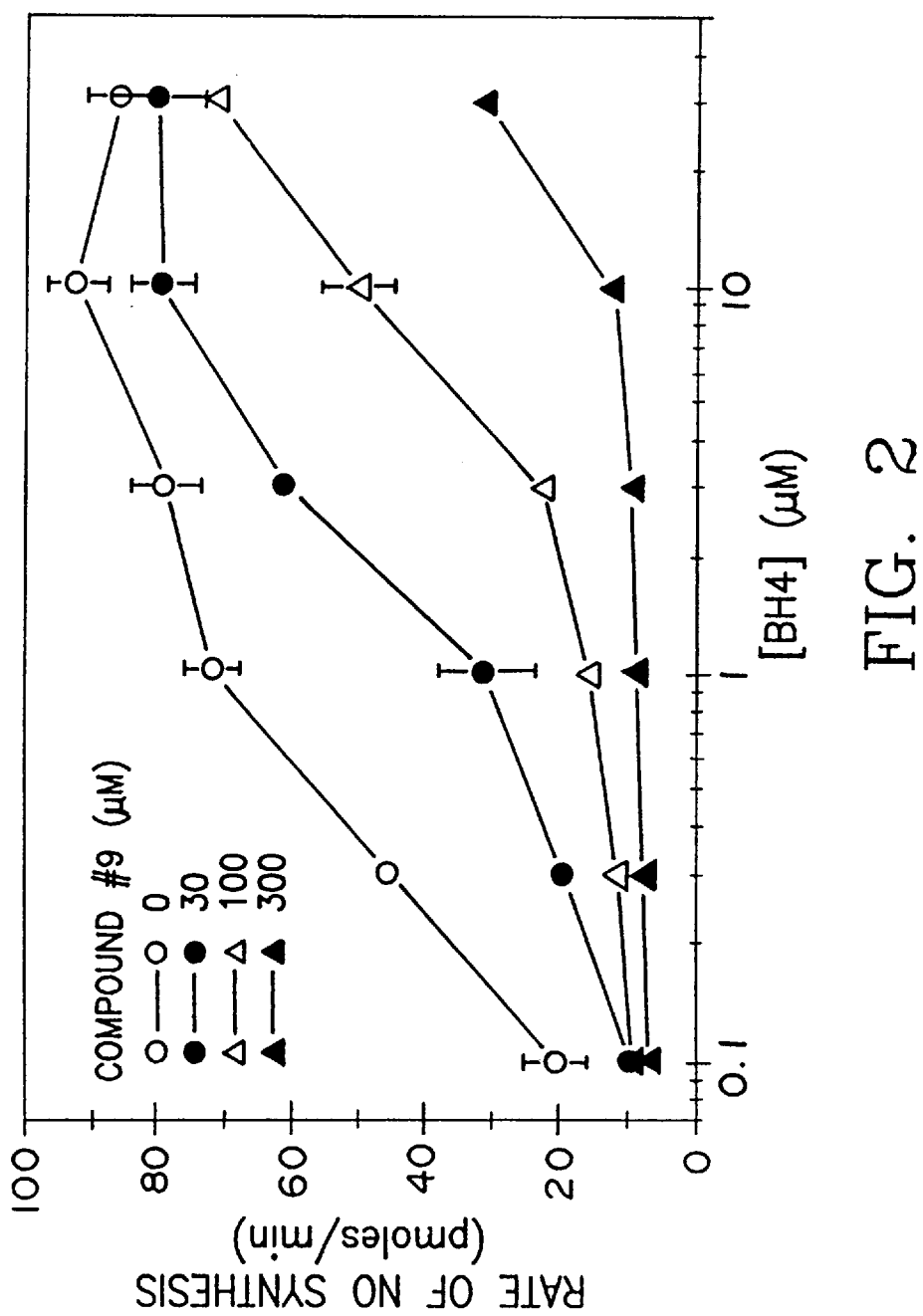
FIG. 2 depicts graphs of rate of nitric oxide (denoted NO) synthesis versus tetrahydrobiopterin (denoted $BH_4$) concentration for denoted concentrations of 1-methyl-4-(3',4'-dihydroxyphenyl)-1,2,3,6-tetrahydropyridine (denoted Compound #9) and shows results of Example II.

An experiment was carried out as in Example I except that varying concentrations of tetrahydrobiopterin were used as shown in FIG. 2 and 1-methyl-4-(3',4'-dihydroxyphenyl)-1,2,3,6-tetrahydropyridine (referred to in FIG. 2 as Compound #9) was used (rather than #5, #6, #7, and #13) at the concentrations indicated in FIG. 2.

The results are shown in FIG. 2.

As shown in FIG. 2, the inhibition by Compound #9 can be prevented by excess tetrahydrobiopterin indicating that the mechanism of inhibition is by interfering with tetrahydrobiopterin utilization.

EXAMPLE III

Figure 3:
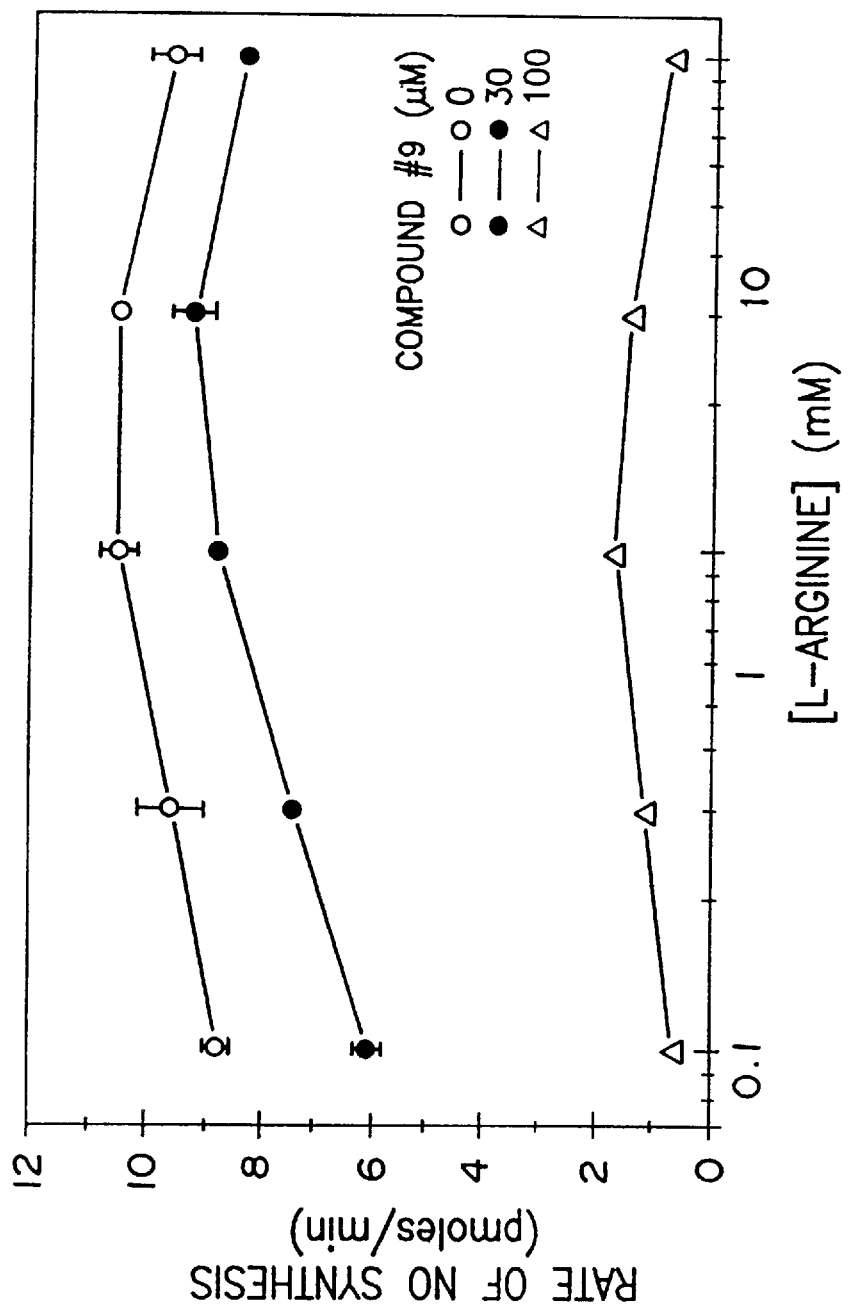
FIG. 3 depicts graphs of rate of nitric oxide (denoted NO) synthesis versus L-arginine concentration for denoted concentrations of 1-methyl-4-(3',4'-dihydroxyphenyl)-1,2,3,6-tetrahydropyridine (denoted Compound #9) and shows results of Example III.

An experiment was carried out as in Example II except that tetrahydrobiopterin concentration was at 10 $\mu$M, the concentration of L-arginine was varied as shown in FIG. 3 and 1-methyl-4-(3',4'-dihydroxyphenyl)-1,2,3,6-tetrahydropyridine (referred to in FIG. 3 as Compound #9) was used at concentrations of 0 $\mu$M, 30 $\mu$M and 100 $\mu$M.

The results are shown in FIG. 3.

As shown in FIG. 3, arginine is not able to overcome the inhibition by Compound #9. This is consistent with the view that this agent interferes with tetrahydrobiopterin utilization rather than with arginine utilization (as is the case for previously described nitric oxide synthase inhibitors such as $N^G$-methyl-L-arginine).

EXAMPLE IV

Aortic smooth muscle cells were cultured by explanting segments of the medial layer of aortae from adult male Fischer 344 rats. Aortae were removed aseptically and freed of adventitial and endothelial cells by scraping both the lumenal and abluminal surfaces. Medial fragments (1–2 mm) were allowed to attach to dry Primaria 25 cm$^2$ tissue culture flasks (Falcon; Oxnard, Calif.) which were kept moist with growth medium until cells emerged. Cultures were fed twice weekly with Medium 199 containing 10% fetal bovine serum, 25 mM HEPES, 2 mM L-glutamine, 40 $\mu$g/ml endothelial cell growth supplement (Biomedical Technologies; Stoughton, Mass.) and 10 $\mu$g/ml gentamycin (GIBCO; Grand Island, N.Y.). When primary cultures became confluent, they are passaged by trypsinization. Cells in passage 10–15 were seeded at 20,000/well. When the cells became confluent (density of 60–80—10$^3$ cells in a well), the medium was removed by aspiration and fresh medium was introduced consisting of 200 $\mu$l of RPMI 1640 (Whittaker Laboratories) containing 10% bovine calf serum, 25 mM HEPES buffer (pH 7.4), 2 mM glutamine, 80 U/ml penicillin, 80 $\mu$g/ml streptomycin, 2 $\mu$g/ml fugizone, 50 ng/ml interferon-gamma and 30 $\mu$g/ml *Escherichia coli* polysaccharide.

Figure 4:
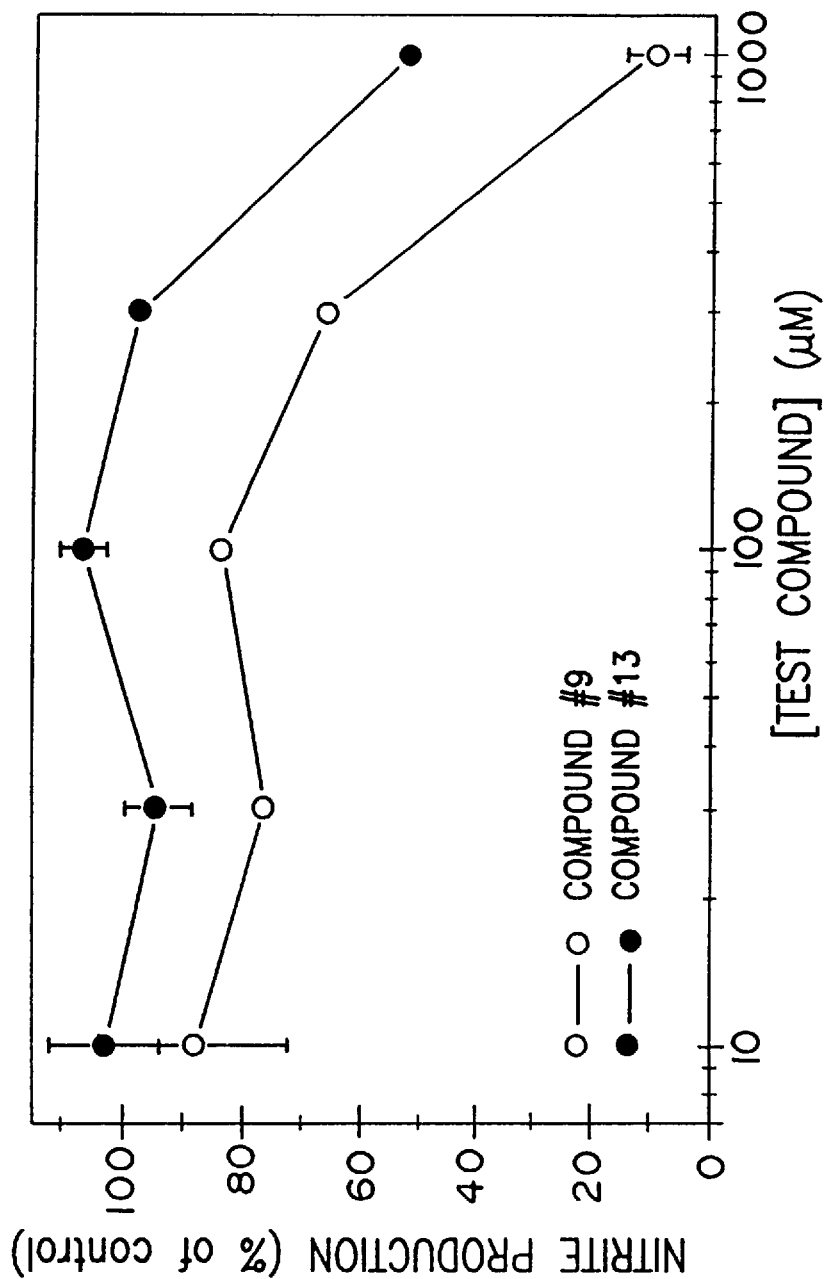
FIG. 4 depicts graphs of nitrite production versus concentration for 1-methyl-4-(3',4'-dihydroxyphenyl)-1,2,3,6-tetrahydropyridine (denoted Compound #9) and 4-(3',4'-dihydroxyphenyl)-1,2,3,6-tetrahydropyridine (denoted Compound #13) and shows results of Example IV.

Compound#9, i.e., 1-methyl-4-(3',4'-dihydroxyphenyl)-1,2,3,6-tetrahydropyridine, and Compound #13, i.e., 4-(3',4'-dihydroxyphenyl)-1,2,3,6-tetrahydropyridine, were added to wells at the concentrations indicated in FIG. 4 and nitrite accumulation in the cell culture medium was quantified after 24 hours. Assaying for nitrite was carried out based on the Griess reaction (Green, L. C., et al, Anal. Biochem. 126: 131–138 (1982)); this involved addition of 100 $\mu$l of reaction medium to 100 $\mu$l of Greiss reagent (0.5% sulfanilamide and 0.05% naphthaline diamine dihydrochloride in 2.5% phosphoric acid) and measuring optical density at 550 nm using a microplate reader (Molecular Devices, Menlo Park, Calif.) and determining nitrite concentrations by comparison of standard solution of sodium nitrite, with background nitrite levels being subtracted from experimental values.

The results are shown in FIG. 4.

The results of FIG. 4 demonstrate that Compound #9 and Compound #13 are inhibitors of immunostimulant induced nitric oxide synthase in vascular smooth muscle cells.

EXAMPLE V

Sprague-Dawley rats are anesthetized with ethyl ether and then pithed as described by Shiply and Tilden. The animals are pithed prior to use in the present experiment so as to eliminate any control of blood pressure by the central nervous system. Animals are given intraperitoneally 15 mg/kg of bacterial lipopolysaccharide (LPS) and after 6 hours are instrumented for blood pressure recording. To record blood pressure, a tracheotomy is first performed on each rat, after which the rats are artificially respired with room air. The left common carotid artery is then cannulated in each rat for blood pressure measurement via a Stratham pressure transducer (Hato Rey, Puerto Rico) and displayed on a physiograph (Grass Instruments, Quincy Mass.). Heart rate is measured from the lead III electrocardiogram. Blood pressure is found to be markedly decreased relative to that in animals which did not receive LPS.

Administration of phenylephrine (5 $\mu$g/kg), intravenously, provides a moderate increase in blood pressure. Intravenous administration of 1-methyl-4-(3',4'-dihydroxyphenyl)-1,2,3,6-tetrahydropyridine (also referred to as Compound #9) at 10 $\mu$g/kg or 4-(3',4'-dihydroxyphenyl)-1,2,3,6-tetrahydropyridine (also referred to as Compound #13) at 10 $\mu$g/kg, in place of the phenylephrine, causes a significant increase in blood pressure.

This shows Compound #9 and Compound #13 are effective at reversing hypotension caused by bacterial lipopolysaccharide, a condition characterized by insensitive, refractory response to conventional $\alpha_1$-adrenergic agonists, such as phenylephrine.

EXAMPLE VI

Nitric oxide synthase enzyme was purified from immunostimulant activated rat aortic smooth muscle cells as described in Example I.

Rate of nitric oxide synthesis was assayed as in Example I.

Incubations were carried out with 0.5 mM L-arginine, 0.5 mM nicotinamide adenine dinucleotide phosphate (reduced form), 10 $\mu$M flavin adenine dinucleotide, 1 $\mu$g purified nitric oxide synthase protein, 80 mM Tris buffer and concentrations of tetrahydropterin analogs as set forth in the Table below. Results are set forth in the Table below wherein "n.d." stands for none detected. All the tetrahydropterin analogs tested were purchased using commercial catalogs. In the absence of any tetrahydrobiopterin analog, nitric oxide synthesis was undetectable.

TABLE

| Tetrahydropterin Analog | Rate of Nitric Oxide Synthesis (pmoles/min) | | |
|---|---|---|---|
| | 2.5 µg/ml | 25 µg/ml | 250 µg/ml |
| (6R)-tetrahydro-L-biopterin | 115.2 ± 13.6 | 107.8 ± 2.2 | 98.2 ± 8.4 |
| (6S)-tetrahydro-L-biopterin | 43.4 ± 1.5 | 61.2 ± 2.9 | 65.9 ± 2.6 |
| (6R,S)-tetrahydropterin | 1.0 ± 0.2 | 20.4 ± 0.2 | 58.4 ± 3.8 |
| (6R,S)-6-methyl-tetrahydropterin | 7.8 ± 0.9 | 32.8 ± 0.9 | 68.9 ± 0.8 |
| (6R,S)-6-hydroxymethyl-tetrahydropterin | 13.5 ± 5.1 | 43.4 ± 2.3 | 79.9 ± 5.6 |
| (6R,S)-6,7-dimethyl-tetrahydropterin | 0.0 ± 0.4 | 0.0 ± 0.3 | 0.0 ± 0.2 |
| (6R,S)-tetrahydro-monapterin | 18.0 ± 0.3 | 54.9 ± 2.7 | 64.1 ± 4.7 |
| (6R,S)-tetrahydro-D-neopterin | 12.2 ± 0.6 | 41.8 ± 1.6 | 58.8 ± 1.3 |
| (7R,S)-tetrahydro-L-primapterin | 3.8 ± 1.4 | 4.2 ± 0.6 | 16.1 ± 1.6 |
| (6R,S)-tetrahydrofolic acid | 0.3 ± 0.2 | 0.2 ± 0.3 | 1.6 ± 1.4 |
| 5-methyl-(6R,S)-tetrahydrofolic acid | 0.0 ± 0.3 | 0.2 ± 0.2 | 0.3 ± 0.4 |
| 5,10-methenyl-(6R,S)-tetrahydrofolic acid | n.d. | n.d. | n.d. |
| (6R,S)—$N^5,N^{10}$-methylene-tetrahydrofolic | n.d. | n.d. | n.d. |

The results set forth in the Table show that the naturally occurring isoform of tetrahydrobiopterin, namely (6R)-tetrahydro-L-biopterin is the most potent cofactor for support of nitric oxide synthesis and the other tetrahydropterin analogs function in varying degrees of efficacy. Five of these did not support nitric oxide synthesis, namely (6R,S)-6,7-dimethyl-tetrahydropterin, (6R,S)-tetrahydrofolic acid, 5-methyl-(6R, S)-tetrahydrofolic acid, 5,10-methenyl-(6R, S)-tetrahydrofolic acid and (6R, S)-$N^5,N^{10}$-methylene-tetrahydrofolic acid. The first two were tested for their ability to inhibit tetrahydrobiopterin activation of nitric oxide synthesis as set forth below.

Reaction medium was made up as above except for varying concentration of tetrahydrobiopterin in the absence or presence of various concentrations of (6R,S)-6,7-dimethyl-tetrahydropterin and (6R,S)-tetrahydrofolic acid. The results for (6R,S)-6,7-dimethyl-tetrahydropterin are shown in FIG. 5. The results for (6R,S)-tetrahydrofolic acid are shown in FIG. 6. As shown in FIGS. 5 and 6, these tetrahydropterin analogs cause concentration dependent inhibition of purified induced nitric oxide synthase from vascular smooth muscle cells.

EXAMPLE VII

Cultured rat aortic smooth muscle cells are induced for nitric oxide synthesis by treatment with bacterial lysopolysaccharide and interferon-gamma as in Example IV, but in one case in the presence of (6R,S)-6,7-dimethyl-tetrahydropterin and in another in the presence of (6R,S)-tetrahydrofolic acid.

Figure 7:
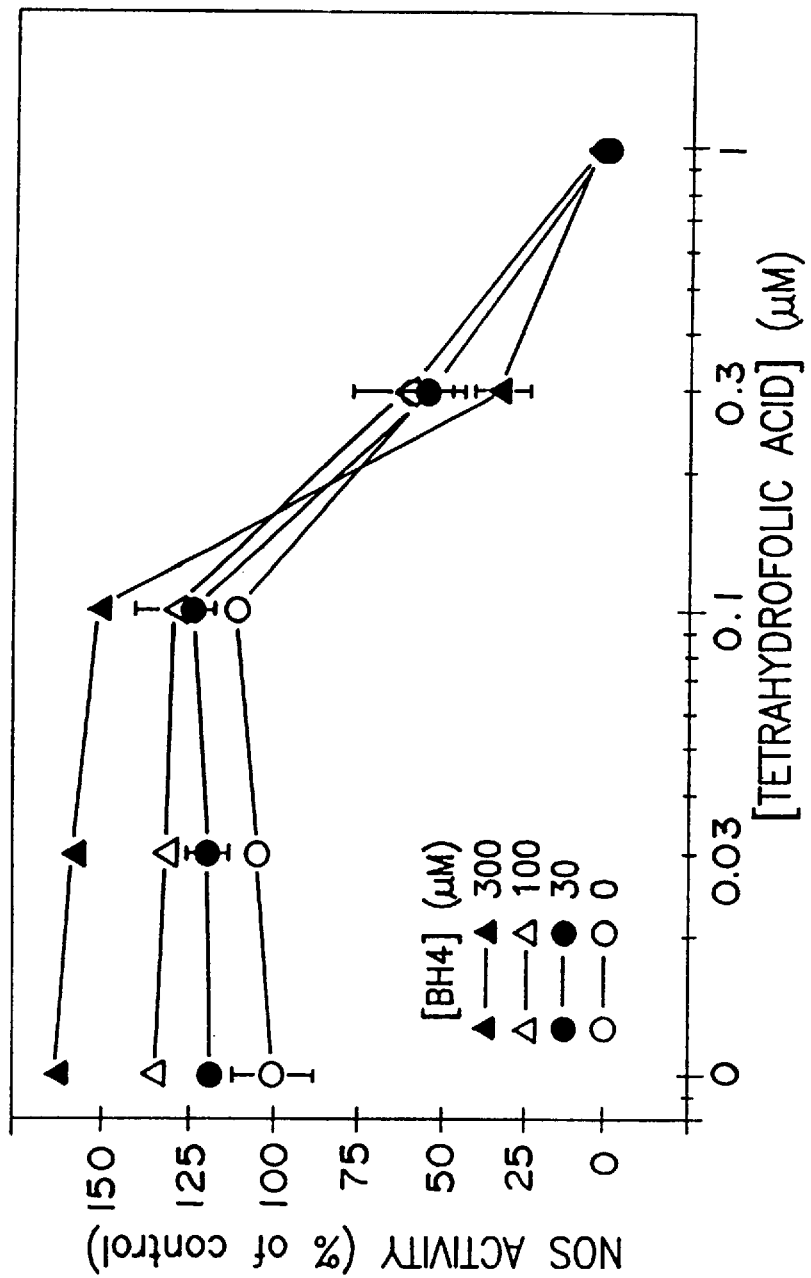
FIG. 7 depicts graphs of nitric oxide synthase (NOS) activity versus tetrahydrofolic acid concentration for denoted concentrations of tetrahydrobiopterin (denoted $BH_4$) and shows results of Example VII.

The results for varying concentrations of (6R,S)-tetrahydrofolic acid with varying concentrations of tetrahydrobiopterin are shown in FIG. 7. The results show that both (6R,S)-6,7-dimethyl-tetrahydropterin and (6R,S)-tetrahydrofolic acid block immunostimulant induced nitric oxide synthesis by intact rat aortic smooth muscle cells.

EXAMPLE VIII

An experiment is carried out as in Example V except that the bacterial lipopolysaccharide treated pithed rats in one case are treated with 300 µg/kg of (6R,S)-6,7-dimethyl-tetrahydropterin and in another case are treated intravenously with 300 µg/kg of (6R,S)-tetrahydrofolic acid in place of the phenylephrine. In both cases the compounds cause a significant increase in blood pressure indicating effectiveness in reversing hypotension caused by bacterial lipopolysaccharide.

EXAMPLE IX

An experiment was carried out as in Example I except that the concentration of tetrahydrobiopterin was fixed at 0.1 µM and the test compounds were 2,4-diamino-6-(diethylamino) pyrimidine, 2,4-diamino-6-morphilino-pyrimidine, 2,4-diamino-6-piperidino-pyrimidine-3-oxide, melanine.hydrochloride salt and 2,4-diamino-6-hydroxypyrimidine and were used in concentrations over the range of 30 µM to 3 mM. The 2,4-diamino-6-(diethylamino)pyrimidine was prepared by the general method set forth hereinbefore. The other test compounds were purchased through commercial channels.

Figure 8:
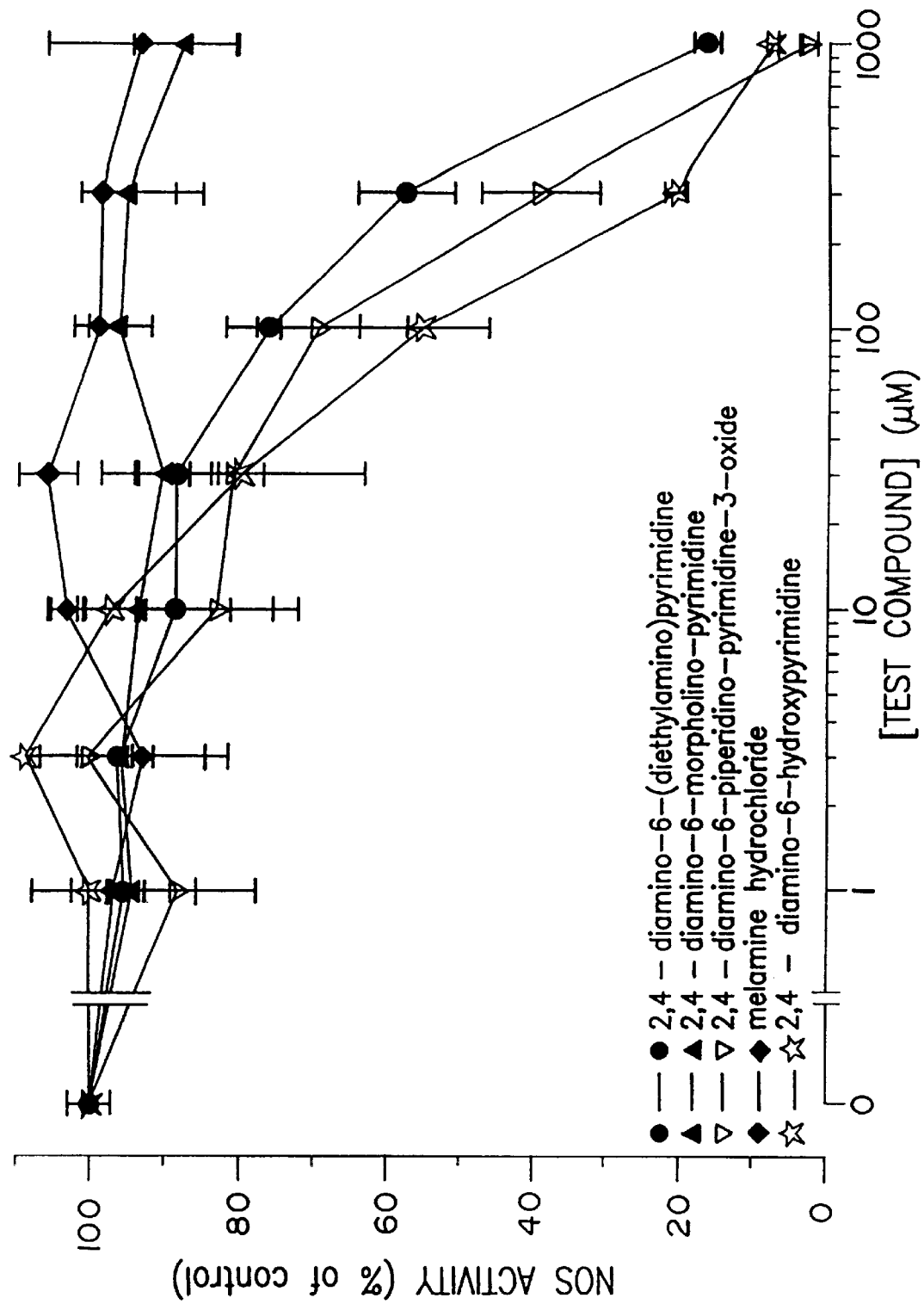
FIG. 8 depicts graphs of nitric oxide synthase (NOS) activity as a percent of control versus concentration for three 2,4-diamino-6-substituted-pyrimidines, 2,4-diamino-6-piperidinopyrimidine-3-oxide and melamine hydrochloride salt and shows results of Example IX.

The results are set forth in FIG. 8.

As shown in FIG. 8, 2,4-diamino-6-(diethylamino) pyrimidine, 2,4-diamino-6-piperidino-pyrimidine-3-oxide and 2,4-diamino-6-hydroxypyrimidine are potent inhibitors of induced nitric oxide synthase.

As shown in FIG. 8, 2,4-diamino-6-morpholino-pyrimidine and melamine.hydrochloride are not inhibitors of induced nitric oxide synthase.

When 4,6-diamino-2-hydroxy-pyrimidine or 2,5-diamino-4,6-dihydroxyprimidine is utilized as a test compound in this example, potent inhibition of induced nitric oxide synthase is noted.

EXAMPLE X

An experiment was carried out as in Example IX except that varying concentrations of tetrahydrobiopterin were used as shown in FIG. 9 and 2,4-diamino-6-hydroxypyrimidine was used at the concentrations indicated in FIG. 9.

The results are shown in FIG. 9.

As shown in FIG. 9, the inhibition by 2,4-diamino-6-hydroxypyrimidine can be overcome by increasing tetrahydrobiopterin concentration indicating that the mechanism for inhibition is by interfering with tetrahydrobiopterin utilization. This is also true for 2,4-diamino-6-(diethylamino)pyrimidine and 2,4-diamino-6-piperidino-pyrimidine-3-oxide and the other pyrimidines that are the subject of the invention herein.

EXAMPLE XI

Cultured rat aortic smooth muscle cells are induced for nitric oxide synthesis by treatment with bacterial lipopolysaccharide and interferon-gamma as in Example IV but in one case in the presence of 1 mM 2,4-diamino-6-(diethylamino)pyrimidine, in another case in the presence of 1 mM 2,4-diamino-6-piperidino-pyrimidine-3-oxide and in still another case in the presence of 1 mM 2,4-diamino-6-hydroxypyrimidine. The results show that all three of the compounds at the concentrations utilized block induced nitric oxide synthesis by intact rat aortic smooth muscle cells. The same results are obtained when the pyrimidine is 1 mM 4,6-diamino-2-hydroxypyrimidine or 1 mM 2,5-diamino-4,6-dihydroxypyrimidine.

EXAMPLE XII

An experiment is carried out as in Example V except that the bacterial lipopolysaccharide treated pithed rats in one case are treated intravenously with 300 mg/kg of 2,4-diamino-6-(diethylamino)pyrimidine, in another case are treated intravenously with 300 mg/kg of 2,4-diamino-6-piperidino-pyrimidine-3-oxide, in another case are treated intravenously with 300 mg/kg of 2,4-diamino-6-hydroxypyrimidine, in another case are treated intravenously with 300 mg/kg of 4,6-diamino-2-hydroxypyrimidine and in still another case are treated intravenously with 300 mg/kg of 2,5-diamino-4,6-dihydroxypyrimidine in place of the phenylephrine. In all cases the compounds cause a significant increase in blood pressure indicating effectiveness in reversing hypotension caused by bacterial lipopolysaccharide.

EXAMPLE XIII

An experiment is carried out as in Example VIII except that the bacterial lipopolysaccharide treated pithed rats in one case are also treated intravenously with 1 mg/kg $N^G$-methyl-L-arginine (to potentiate effectiveness of the (6R,S)-6,7-dimethyl-tetrahydropterin and (6R,S)-tetrahydrofolic acid) and in another case are also treated intravenously with 20 mg/kg of $N^G$-methyl-L-arginine (concurrent therapy). In all cases there is a greater increase in blood pressure than is obtained in Example VIII.

EXAMPLE XIV

An experiment is carried as in Example XII except that the bacterial lipopolysaccharide treated pithed rats in one case are also treated intravenously with 1 mg/kg $N^G$-methyl-L-arginine (to potentiate the effectiveness of the 2,4-diamino-6-(diethylamino)pyrimidine, the 2,4-diamino-6-piperidino-pyrimidine-3-oxide, the 2,4-diamino-6-hydroxypyrimidine, the 4,6-diamino-2-hydroxypyrimidine and the 2,5-diamino-4,6-dihydroxypyrimidine) and in another case are also treated intravenously with 20 mg/kg of $N^g$-methyl-L-arginine (concurrent therapy). In all cases there is a greater increase in blood pressure than is obtained in Example XII.

EXAMPLE XV

Pithed Sprague-Dawley rats are injected intraperitoneally with bacterial lipopolysaccharide (15 mg/kg) and after three hours are given a bolus injection of phenylephrine (6 μg/kg) or a bolus injection of (6R,S) 6,7-dimethyl-tetrahydropterin (300 μg/kg) or (6R,S)-tetrahydrofolic acid (300 μg/kg) and immediately afterward a bolus injection of phenylephrine (6 μg/kg). There is a greater and more prolonged increase in blood pressure where both tetrahydropterin analog and phenylephrine are given.

When 300 mg/kg of 2,4-diamino-6-(diethylamino) pyrimidine or 300 mg/kg of 2,4-diamino-6-piperidino-pyrimidine-3-oxide or 300 mg/kg of 2,4-diamino-6-hydroxypyrimidine or 300 mg/kg of 4,6-diamino-2-hydroxypyrimidine or 300 mg/kg of 2,5-diamino-4,6-dihydroxypyrimidine is substituted for the tetrahydropterin analog, similar results of greater and more prolonged increase in blood pressure are obtained where both the inhibitor and phenylephrine are given compared to where only phenylephrine or only inhibitor is given.

In an alternative herein, the inhibitor of the use of tetrahydrobiopterin as a cofactor for nitric oxide synthase is such inhibitor which is different from 2,4-diamino-6-hydroxypyrimidine.

Many variations of the above will be obvious to those skilled in the art. Thus, the invention is defined by claims.

What is claimed is:

1. A prophylactic or treatment method for systemic hypotension induced by cytokine therapy or exposure to bacterial endotoxin, wherein a subject is treated with a therapeutically effective amount of a nitric oxide synthase inhibitor wherein said inhibitor is an inhibitor of the binding of tetrahydrobiopterin to nitric oxide synthase and said therapeutically effective amount is an amount sufficient to limit the overproduction of nitric oxide from arginine in vascular cells and said inhibitor is not 2,4-diamino-6-hydroxypyrimidine.

2. The method of claim 1 wherein said inhibitor is a tetrahydropterin analog which does not replace tetrahydrobiopterin as a cofactor for nitric oxide synthase.

3. The method of claim 2 wherein said inhibitor is (6R,S)-6,7-dimethyl-tetrahydropterin.

4. The method of claim 2 wherein said inhibitor is (6R,S)-tetrahydrofolic acid.

5. A prophylactic or treatment method for systemic hypotension induced by cytokine therapy or exposure to bacterial endotoxin, wherein a subject is treated with a therapeutically effective amount of a nitric oxide synthase inhibitor wherein said inhibitor is an inhibitor of the binding of tetrahydrobiopterin to nitric oxide synthase and said therapeutically effective amount is an amount sufficient to limit the overproduction of nitric oxide from arginine in vascular cells and said inhibitor is selected from the group consisting of 2,4diamino-, 4,6-diamino-, and 2,5-diamino- mono- and disubstituted pyrimidines and the corresponding pyrimidine-3-oxides and is not 2,4-diamino-6-hydroxypyrimidine.

6. The method of claim 5 wherein said inhibitor is selected from the group consisting of 2,4-diamino-, 4,6-diamino-, and 2,5-diamino- mono- and disubstituted pyrimidines.

7. The method of claim 5 wherein said inhibitor is 2,4-diamino-6-(diethylamino)pyrimidine.

8. The method of claim 5 wherein said inhibitor is 2,4-diamino-6-piperidino-pyrimidine-3-oxide.

9. The method of claim 6 wherein said inhibitor is 2,4-diamino-6-hydroxypyrimidine.

10. The method of claim 6 wherein said inhibitor is 4,6-diamino-2-hydroxypyrimidine.

11. The method of claim 6 wherein said inhibitor is 2,5-diamino-4,6-dihydroxypyrimidine.

12. A prophylactic or treatment method for systemic hypotension induced by cytokine therapy or exposure to bacterial endotoxin, wherein a subject is treated with an $\alpha_1$-adrenergic agonist and a therapeutically effective amount of a nitric oxide synthase inhibitor wherein said inhibitor is an inhibitor of the binding of tetrahydrobiopterin to nitric oxide synthase and said therapeutically effective amount is an amount sufficient to limit the overproduction of nitric oxide from arginine in vascular cells and said inhibitor is a tetrahydrobiopterin analog which does not replace tetrahydrobiopterin as a cofactor for nitric oxide synthase and is not 2,4-diamino-6-hydroxypyrimidine.

13. A prophylactic or treatment method for systemic hypotension induced by cytokine therapy or exposure to bacterial endotoxin, wherein a subject is treated with an $\alpha_1$-adrenergic agonist and a therapeutically effective amount of a nitric oxide synthase inhibitor wherein said inhibitor is an inhibitor of the binding of tetrahydrobiopterin to nitric oxide synthase and said therapeutically effective amount is an amount sufficient to limit the overproduction of nitric oxide from arginine in vascular cells and said inhibitor is selected from the group consisting of 2,4-diamino-, 4,6-diamino-, and 2,5-diamino- mono- and disubstituted pyrimidines and the corresponding pyrimidine-3-oxides.

14. A prophylactic or treatment method for systemic hypotension induced by cytokine therapy or exposure to bacterial endotoxin, wherein a subject is treated with a therapeutically effective amount of a nitric oxide synthase inhibitor wherein said inhibitor is an inhibitor of the binding of tetrahydrobiopterin to nitric oxide synthase and a therapeutically effective amount of a nitric oxide synthase inhibitor which is an arginine or citrulline analog and said therapeutically effective amounts are amounts sufficient to limit the overproduction of nitric oxide from arginine in vascular cells and said inhibitor of the binding of tetrahydrobiopterin to nitric oxide synthase is a tetrahydrobiopterin analog which does not replace tetrahydrobiopterin as a cofactor for nitric oxide synthase and is not 2,4-diamino-6-hydroxypyrimidine.

15. A prophylactic or treatment method for systemic hypotension induced by cytokine therapy or exposure to bacterial endotoxin, wherein a subject is treated with a therapeutically effective amount of a nitric oxide synthase inhibitor wherein said inhibitor is an inhibitor of the binding of tetrahydrobiopterin to nitric oxide synthase and a therapeutically effective amount of a nitric oxide synthase inhibitor which is an arginine or citrulline analog and said therapeutically effective amounts are amounts sufficient to limit the overproduction of nitric oxide from arginine in vascular cells and said inhibitor of the binding of tetrahydrobiopterin to nitric oxide synthase is selected from the group consisting of 2,4-diamino-, 4,6-diamino-, and 2,5-diamino- mono- and disubstituted pyrimidines and the corresponding pyrimidine-3-oxides.

\* \* \* \* \*

UNITED STATES PATENT AND TRADEMARK OFFICE
CERTIFICATE OF CORRECTION

| | | |
|---|---|---|
| PATENT NO. | : 5,874,433 | Page 1 of 1 |
| APPLICATION NO. | : 08/574654 | |
| DATED | : February 23, 1999 | |
| INVENTOR(S) | : Steven S. Gross | |

It is certified that error appears in the above-identified patent and that said Letters Patent is hereby corrected as shown below:

In column 1, lines 7-9, replace:

"This invention was made at least in part with Government support under Grant HL46403 from the National Institutes of Health."

with:

-- This invention was made with Government support under Contract Numbers HL46403 and HL34215 from the National Institutes of Health --.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 5,874,433
APPLICATION NO. : 08/574654
DATED : February 23, 1999
INVENTOR(S) : Steven S. Gross It is certified that error appears in the above-identified patent and that said Letters Patent is hereby corrected as shown below:

In column 1, lines 7-9, replace:

"This invention was made at least in part with Government support under Grant HL46403 from the National Institutes of Health."

with:

-- This invention was made with Government support under Contract Number HL46403 from the National Institutes of Health. The government has certain rights in the invention. --.

This certificate supersedes the Certificate of Correction issued October 7, 2008.

Signed and Sealed this

Tenth Day of February, 2009

JOHN DOLL
*Acting Director of the United States Patent and Trademark Office*